United States Patent [19]
Lesher et al.

[11] Patent Number: 4,524,149
[45] Date of Patent: Jun. 18, 1985

[54] 5-ALKANOYL-6-ALKYL-2(1H)-PYRIDINONES, THEIR PREPARATION AND THEIR CARDIOTONIC USE

[75] Inventors: George Y. Lesher, Schodack; Baldev Singh, East Greenbush, both of N.Y.

[73] Assignee: Sterling Drug Inc., New York, N.Y.

[21] Appl. No.: 464,690

[22] Filed: Feb. 7, 1983

Related U.S. Application Data

[63] Continuation-in-part of Ser. No. 357,872, Mar. 15, 1982, Pat. No. 4,412,077.

[51] Int. Cl.[3] .................. C07D 213/57; C07D 213/50; A61K 31/44

[52] U.S. Cl. .................................... 514/350; 546/288; 546/298; 560/170

[58] Field of Search ................. 546/288, 298; 424/263

[56] References Cited

U.S. PATENT DOCUMENTS 3,654,291 4/1972 Witzel et al. ........................ 546/297
4,412,077 10/1983 Lesher et al. ....................... 546/298

OTHER PUBLICATIONS

Sunthankar et al., Chemical Abstracts, vol. 80, No. 23, Abst. No. 133,202r, June 10, 1974.
Sunthankar et al., [Indian J. of Chem. 11, 1315–16, (1973)].
Kato et al., [J. Heterocyclic Chem. 18, 603–606, (1981)].
Kato et al., [Chem. Pharm. Bull. 17, 2411–2416, (1969)].
Fujita, [Chem. Pharm. Bull. 23, 501–506, (1975)].
Krasnaya et al., [C.A. 87, 68099r, (1977)].

*Primary Examiner*—Alan L. Rotman
*Attorney, Agent, or Firm*—Robert K. Bair; B. Woodrow Wyatt; Paul E. Dupont

[57] ABSTRACT

4-$R_2$-5-(Lower-alkanoyl)-6-(lower-alkyl)-2(1H)-pyridinones (I), useful as cardiotonics, where $R_2$ is hydrogen or methyl, are prepared by reacting 2-(lower-alkanoyl)-1-(lower-alkyl)ethenamine (II) with lower-alkyl 2-propynoate or 2-butynoate respectively or by hydrolyzing 4-$R_2$-5-(lower-alkanoyl)-6-(lower-alkyl)-1,2-dihydro-2-oxonicotinonitrile (III), Q is CN) or corresponding 4-$R_2$-5-(lower-alkanoyl)-6-(lower-alkyl)-1,2-dihydro-2-oxonicotinamide to produce the corresponding 5-(lower-alkanoyl)-6-(lower-alkyl)-1,2-dihydro-2-oxonicotinic acid and decarboxylating said substituted nictotinic acid to produce I. Also disclosed and claimed are cardiotonic uses of 3-Q-4-$R_2$-5-(lower-alkanoyl)-6-(lower-alkyl)-2(1H)-pyridinones where Q is hydrogen or cyano and $R_2$ is hydrogen or methyl (III). Also shown and claimed is methyl 4-acetyl-5-amino-2,4-hexadienoate or acid-addition salt thereof, useful as intermediate or cardiotonic.

19 Claims, No Drawings

5-ALKANOYL-6-ALKYL-2(1H)-PYRIDINONES, THEIR PREPARATION AND THEIR CARDIOTONIC USE

CROSS-REFERENCE TO RELATED APPLICATION

This application is a continuation-in-part of copending application Ser. No. 357,872, filed Mar. 15, 1982 and now U.S. Pat. No. 4,412,077 issued Oct. 25, 1983.

BACKGROUND OF THE INVENTION (a) Field of the Invention

This invention relates to alkanoylpyridinones, their preparation and their use as cardiotonics.

(b) Description of the Prior Art

Sunthankar et al. [Indian J. of Chemistry 11, 1315–16 (1973)] show the reaction of cyanoacetamide with conjugated enol ethers, such as ethoxymethylenemalonate and analogous conjugated enol ethers to produce various substituted 2-pyridinones including 5-acetyl-1,2-dihydro-6-methyl-2-oxo-3-pyridinecarbonitrile and 5-acetyl-1,2-dihydro-6-methyl-2-oxo-3-pyridinecarboxamide. No utility is shown for these compounds.

Kato et al. [J. Heterocyclic Chem. 18, 603–606 (1981)] show, inter alia, the dehydrogenation of 5-acetyl-3,4-dihydro-6-methyl-2(1H)-pyridinone by heating it with palladium black to produce 5-acetyl-6-methyl-2(1H)-pyridinone, which in turn is reacted with phosphorus oxychloride (phosphoryl chloride) to produce a mixture of 6-chloro-3-ethynyl-2-methylpyridine and 6-chloro-3-(1-chlorovinyl)-2-methylpyridine.

Kato et al. [Chem. Pharm. Bull. 17, 2411–2416 (1969)] disclose the preparation of 5-acetyl-3,4-dihydro-6-methyl-2(1H)-pyridinone in two ways: (a) by refluxing 4-oxo-2-penten-2-amine and acrylic anhydride in chloroform (75% yield); and (b) by heating 4-oxo-2-penten-2-amine and ethyl acrylate in ethanol containing sodium ethoxide (9% yield).

Example 13 of U.S. Pat. No. 3,654,291, issued April 4, 1972, shows the reaction of 3-cyano-6-methyl-2(1H)-pyridinone with methylmagnesium iodide in benzene to produce 3-acetyl-6-methyl-2(1H)-pyridinone, which is then used as an intermediate to prepare the corresponding 3-acetyl-6-methyl-5-nitro-2(1H)-pyridinone, in turn, an intermediate for preparing the corresponding 5-amino compound, also used as an intermediate.

Fujita [Chem. Pharm. Bull. 23, 501–506 (1975)] in a chemical paper reporting the results of acylation of 1-alkyl-2(1H)-pyridinones by various means shows the preparation of various 5-acyl- and 3,5-diacyl-1-alkyl-2(1H)-pyridinones, including 5-acetyl-1-methyl-2(1H)-pyridinone and its 5-(RCO) homologs where R is $C_2H_5$, $C_3H_7$ and $C_4H_9$. No pharmaceutical properties of these compounds are disclosed.

Krasnaya et al [C.A. 87, 68099r (1977)] show, inter alia, the use of derivatives of ethyl 2-acetyl-5-amino-2,4-pentadienoate as an intermediate.

SUMMARY OF THE INVENTION

In a composition of matter aspect, the invention resides in 4-$R_2$-5-(lower-alkanoyl)-6-(lower-alkyl)-2(1H)-pyridinones, which are useful as cardiotonic agents, where $R_2$ is hydrogen or methyl.

The invention in a process aspect comprises reacting 2-(lower-alkanoyl)-1-(lower-alkyl)ethenamine with a lower-alkyl 2-propynoate or 2-butynoate to produce 5-(lower-alkanoyl)-6-(lower-alkyl)-2(1H)-pyridinone or 5-(lower-alkanoyl)-6-(lower-alkyl)-4-methyl-2(1H)-pyridinone.

A composition aspect of the invention resides in a cardiotonic composition for increasing cardiac contractility in a patient, said composition comprising a pharmaceutically acceptable carrier and, as the active ingredient thereof, a cardiotonically effective amount of 3-Q-4-$R_2$-5-(lower-alkanoyl)-6-(lower-alkyl)-2(1H)-pyridinone, where Q is hydrogen or cyano and $R_2$ is hydrogen or methyl.

In a method aspect, the invention relates to a method for increasing cardiac contractility in a patient requiring such treatment which comprises the administration of a medicament comprising a pharmaceutically acceptable carrier and, as the active component thereof, a cardiotonically effective amount of 3-Q-4-$R_2$-5-(lower-alkanoyl)-6-(lower-alkyl)-2(1H)-pyridinone, where Q is hydrogen or cyano and $R_2$ is hydrogen or methyl.

In another process aspect, the invention resides in hydrolyzing 4-$R_2$-5-(lower-alkanoyl)-6-(lower-alkyl)-1,2-dihydro-2-oxo-nicotinonitrile to produce the corresponding substituted nicotinic acid and decarboxylating said nicotinic acid to produce 4-$R_2$-5-(lower-alkanoyl)-6-(lower-alkyl)-2(1H)-pyridinone.

Another composition of matter aspect of the invention resides in 6-ethyl-1,2-dihydro-2-oxo-5-(n-propanoyl)-nicotinonitrile.

Another composition of matter aspect of the invention resides in methyl 4-acetyl-5-amino-2,4-hexadienoate or acid-addition salt thereof.

DETAILED DESCRIPTION INCLUSIVE OF PREFERRED EMBODIMENTS

In a composition of matter aspect the invention resides in 4-$R_2$-5-(lower-alkanoyl)-6-(lower-alkyl)-2(1H)-pyridinone having formula I

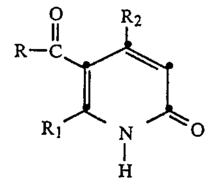

I where R and $R_1$ are each lower-alkyl and $R_2$ is hydrogen or methyl. The compounds of formula I are useful as cardiotonic agents, as determined by standard pharmacological evaluation procedures. Preferred embodiments are those of formula I where $R_2$ is hydrogen, $R_1$ is methyl or ethyl and R is methyl, ethyl or propyl.

In one process aspect the invention resides in the process which comprises reacting 2-(lower-alkanoyl)-1-(lower-alkyl)ethenamine of formula II

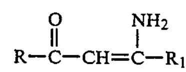

II where R and $R_1$ are each lower-alkyl, with lower-alkyl 2-propynoate or 2-butynoate to produce the compound of formula I where $R_2$ is hydrogen or methyl respectively. Preferred embodiments are those using methyl or ethyl 2-propynoate and the ethenamine derivative (II) where R is methyl, ethyl or propyl and $R_1$ is methyl or ethyl.

A composition aspect of the invention resides in a cardiotonic composition for increasing cardiac contractility, said composition comprising a pharmaceutically acceptable carrier and, as the active component thereof, a cardiotonically effective amount of 3-Q-4-$R_2$-5-(lower-alkanoyl)-6-(lower-alkyl)-2(1H)-pyridinone having formula III

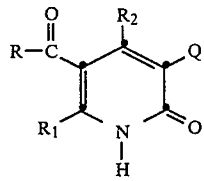

III where Q is hydrogen or cyano, R and $R_1$ are each lower-alkyl and $R_2$ is hydrogen or methyl. Preferred embodiments are said compounds of formula III where Q is hydrogen, $R_2$ is hydrogen, $R_1$ is methyl or ethyl and R is methyl, ethyl or propyl and where Q is cyano, $R_2$ is hydrogen and $R_1$ and R are each ethyl.

A method aspect of the invention resides in the method for increasing cardiac contractility in a patient requiring such treatment which comprises administering orally or parenterally in a solid or liquid dosage form to such patient a cardiotonically effective amount of 3-Q-4-$R_2$-5-(lower-alkanoyl)-6-(lower-alkyl)-2(1H)-pyridinone of formula III where Q is hydrogen or cyano and $R_2$ is hydrogen or methyl. Preferred embodiments of this method aspect are those using the abovesaid composition embodiments where Q is hydrogen, $R_2$ is hydrogen, $R_1$ is methyl or ethyl and R is methyl, ethyl or propyl and where Q is cyano, $R_2$ is hydrogen and $R_1$ and R are each ethyl.

Another process of the invention resides in the process which comprises hydrolyzing 4-$R_2$-5-(lower-alkanoyl)-6-(lower-alkyl)-1,2-dihydro-2-oxonicotinonitrile of formula III where Q is cyano or corresponding 4-$R_2$-5-(lower-alkanoyl)-6-(lower-alkyl)-1,2-dihydro-2-oxonicotinamide to produce the corresponding 4-$R_2$-5-(lower-alkanoyl)-6-(lower-alkyl)-1,2-dihydro-2-oxonicotinic acid and decarboxylating said substituted-nicotinic acid to produce the 4-$R_2$-5-(lower-alkanoyl)-6-(lower-alkyl)-2(1H)-pyridinone of formula I. Preferred aspects of this process are those using said substituted-nicotinonitrile where $R_2$ is hydrogen, lower-alkanoyl is acetyl, n-propanoyl or butanoyl and lower-alkyl is methyl or ethyl.

Another composition of matter aspect of the invention resides in 6-ethyl-1,2-dihydro-2-oxo-5-(n-propanoyl)-nicotinonitrile, which is useful as a cardiotonic agent as determined by standard pharmacological evaluation procedures.

Another composition of matter aspect of the invention resides in methyl 4-acetyl-5-amino-2,4-hexadienoate or acid-addition salt thereof, which is useful as an intermediate and as a cardiotonic agent as determined by standard pharmacological evaluation procedures. Its acid-addition salt is prepared by conventional means using a known inorganic or organic acid. Preferred salts for cardiotonic use are pharmaceutically acceptable acid-addition salts, e.g., hydrochloride, methanesulfonate, lactate, sulfate or phosphate.

The term "lower-alkyl" as used herein, e.g., as the meaning for $R_1$ or R in formula I, means alkyl radicals having from one to four carbon atoms which can be arranged as straight or branched chains, illustrated by methyl, ethyl, n-propyl, isopropyl, n-butyl, sec.-butyl, tert.-butyl and isobutyl. Thus, the term "lower-alkanoyl" as used herein is (lower-alkyl)-carbonyl, i.e.,

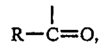

as used in each of formulas I, II and III.

The molecular structures of the compounds of formula I or III or other composition of matter aspects of the invention were assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same.

The preparation of 5-(lower-alkanoyl)-6-(lower-alkyl)-2(1H)-pyridinone or 5-(lower-alkanoyl)-6-(lower-alkyl)-4-methyl-2(1H)-pyridinone is carried out by heating at about 100° C. to 150° C. 2-(lower-alkanoyl)-1-(lower-alkyl)ethanamine of formula II with a lower-alkyl, preferably methyl or ethyl, 2-propynoate or 2-butynoate, respectively, with or without a suitable solvent.

The intermediate 2-(lower-alkanoyl)-1-(lower-alkyl)-ethenamines of formula II are generally known compounds which are prepared by conventional means, as illustrated hereinbelow in the specific exemplary disclosure.

The 4-$R_2$-5-(lower-alkanoyl)-6-(lower-alkyl)-1,2-dihydro-2-oxonicotinonitriles of formula III where Q is cyano or corresponding 4-$R_2$-5-(lower-alkanoyl)-6-(lower-alkyl)-1,2-dihydro-2-oxonicotinamides are conveniently hydrolyzed to produce the correspondingly substituted-nicotinic acids under aqueous acidic conditions by heating with aqueous mineral acid, preferably sulfuric acid and preferably at about 70° C. to 130° C. Alternatively, this hydrolysis can be carried out under aqueous alkaline conditions, preferably using aqueous sodium or potassium hydroxide at about 95°-100° C.

Decarboxylation of the 4-$R_2$-5-(lower-alkanoyl)-6-(lower-alkyl)-1,2-dihydro-2-oxonicotinic acids to produce the corresponding 4-$R_2$-5-(lower-alkanoyl)-6-(lower-alkyl)-2(1H)-pyridinones of formula I is carried out by heating in the absence or presence of a suitable inert solvent at about 240° C. to 280° C., preferably at about 245° C. to 250° C.

The 4-$R_2$-5-(lower-alkanoyl)-6-(lower-alkyl)-1,2-dihydro-2-oxonicotinonitriles of formula III where Q is cyano or 4-$R_2$-5-(lower-alkanoyl)-6-(lower-alkyl)-1,2-dihydro-2-oxonicotinamides are prepared by a generally known method (Sunthankar et al., supra) or an improved modification thereof, as illustrated hereinbelow in the specific exemplary disclosure.

The following examples will further illustrate the invention without, however, limiting it thereto.

A. 5-(LOWER-ALKANOYL)-6-(LOWER-ALKYL)-1,2-DIHYDRO-2-OXONICOTINONITRILES

A-1. 5-Acetyl-1,2-dihydro-6-methyl-2-oxonicotinonitrile—A solution containing 60 g of dimethylformamide dimethyl acetal and 50 g of 2,4-pentanedione was heated on a steam bath for 2.5 hours and cooled. To the resulting solution containing 3-dimethylaminomethylene-2,4-pentanedione was added 300 ml of methanol, 27 g of sodium methoxide and 47 g of cyanoacetamide. The resulting mixture was heated on a steam bath for 4 hours, the hot solution poured into 700 ml of water and the aqueous mixture acidified with acetic acid and chilled in an ice bath. The solid that separated was collected, dried, and heated with 400 ml. of methanol. Insoluble material was filtered from the hot methanol mixture and the filtrate cooled. The product that separated was collected and dried at 90° C. to produce 24.6 g of 5-acetyl-1,2-dihydro-6-methyl-2-oxonicotinonitrile, m.p. 227°-230° C. [Sunthankar et al., supra, m.p. 231° C.]

A-2. 6-Ethyl-1,2-dihydro-2-oxo-5-(n-propanoyl)-nicotinonitrile—To a stirred mixture containing 200 ml of dimethylformamide and 128 g of 3,5-heptanedione was added 134 ml of dimethylformamide dimethyl acetal over a 15 minute period and the resulting mixture was allowed to stand at room temperature overnight. The reaction mixture was then heated on a steam bath for 1 hour and concentrated on a rotary evaporator to a constant weight of 186.4 g, as a deep yellow oil, of 4-dimethylaminomethylene-3,5-heptanedione. To a stirred mixture containing 186.4 g of 4-dimethylaminomethylene-3,5-heptanedione, 92 g of cyanoacetamide and 1200 ml of methanol was added over a ten minute period 57 g of sodium methoxide, whereupon a mild exothermic reaction took place. The resulting mixture was refluxed for 2.5 hours, cooled and the methanol evaporated using a rotary evaporator. To the yellow residue was added 1 liter of water and 80 ml of glacial acetic acid. The separated white solid was collected, washed with water and dried in a vacuum oven at 90°-95° C. to yield 161 g of 6-ethyl-1,2-dihydro-2-oxo-5-(n-propanoyl)nicotinonitrile, m.p. 243°-245° C. This sample was used in the subsequent hydrolysis step described in Example B-2 to produce the corresponding nicotinic acid derivative. A 12 g sample of the nicotinonitrile was recrystallized from ethanol in quantitative yield to give the compound, as fine white needles, m.p. 245°-246° C.

A-3. 5-(n-Butanoyl)-1,2-dihydro-2-oxo-6-n-propylnicotinonitrile, m.p. 205°-207° C., 25.4 g, was prepared following the procedure described in Example A-2 first using 25 g of 4,6-nonanedione, 25 ml of dimethylformamide dimethyl acetal and 25 ml of dimethylformamide to yield, as an oil, 41 g of 5-(dimethylaminomethylene-4,6-nonanedionedione and then refluxing said dione with a mixture containing 14.3 g of cyanoacetamide, 300 ml of methanol and 9.3 g of sodium methoxide, evaporating the reaction mixture to dryness, dissolving the residue in 200 ml of water, acidifying with acetic acid, collecting and drying the product, and recrystallizing the 30.4 g of product from isopropyl alcohol.

A-4. 1,2-Dihydro-6-methyl-2-oxo-5-(n-propanoyl)-nicotinonitrile and 5-acetyl-6-ethyl-1,2-dihydro-2-oxonicotinonitrile—A mixture containing 34 g of 2,4-hexanedione, 50 ml of dimethylformamide and 40 ml of dimethylformamide dimethyl acetal was allowed to stand at room temperature overnight and then concentrated on a rotary evaporator at steam bath temperature to yield, as a liquid, 3-dimethylaminomethylene-2,4-hexanedione. A mixture containing said 3-dimethylaminomethylene-2,4-hexanedione, 300 ml of methanol 25.2 g of cyanoacetamide and 16.2 g of sodium methoxide was refluxed with stirring for 3 hours and then concentrated in vacuo to remove the methanol. The residue was dissolved in 300 ml of warm water and filtered. The filtrate was acidified with acetic acid and the resulting precipitate was collected, washed with water, dried in vacuo at 90°-95° C. and recrystallized from dimethylformamide (75 ml) to yield 7.8 g of 1,2-dihydro-6-methyl-2-oxo-5-(n-propanoyl)nicotinonitrile, m.p. 265°-268° C. with decomposition the acidic mother liquor was concentrated to dryness and digested with hot methanol and cooled. The separated solid was dried, 20.2 g, and recrystallized from dimethylformamide to yield 9.8 g of finely crystalline material, m.p. 259°-263° C. with decomposition. The NMR spectral data for this compound indicated it to be mostly said 1,2-dihydro-6-methyl-2-oxo-5-(n-propanoyl)nicotinonitrile. The resulting mother liquors were combined and concentrated on a rotary evaporator and the resulting residue was recrystallized from ethanol to yield 20.4 g of solid, m.p. 220°-226° C. The NMR spectral data for this solid indicated it to be a 5:4 mixture of said 1,2-dihydro-6-methyl-2-oxo-5-(n-propanoyl)nicotinonitrile and 5-acetyl-6-ethyl-1,2-dihydro-2-oxonicotinonitrile. Preliminary attempts to separate the two compounds by fractional crystallization were unsuccessful; however, the two compounds should be separable.

A-5. 5-Acetyl-1,2-dihydro-6-methyl-2-oxonicotinonitrile and 5-acetyl-1,2-dihydro-6-methyl-2-oxonicotinamide—A mixture containing 200 g of 2,4-pentanedione and 300 ml of dimethylformamide dimethyl acetal was heated under reflux on a steam bath for 5 hours and then allowed to stand at room temperature overnight. The excess solvent was distilled off using a rotary evaporator to a constant weight of 307 g, as an oil, of 3-dimethylaminomethylene-2,4-pentanedione which was combined with 700 ml of methanol and 168 g of cyanoacetamide followed by 108 g of sodium methoxide with stirring and cooling. The reaction mixture was heated under reflux for 7 hours, cooled and treated with 150 ml of glacial acetic acid. The separated solid was collected and the filtrate evaporated to dryness. The residue was treated with 700 ml of water and the insoluble material was collected, washed with water and dried. The two solids were combined and refluxed with 1 liter of methanol. The insoluble beige solid was collected, washed with hot methanol and dried in vacuo at 90°-95° C. to yield 55.8 g of 5-acetyl-1,2-dihydro-6-methyl-2-oxonicotinamide, m.p. >320° C. Both filtrates were concentrated to a volume of about 800 ml and cooled. The separated solid was collected and dried in vacuo at 90°-95° C. to yield 100 g of 5-acetyl-1,2-dihydro-6-methyl-2-oxonicotinonitrile, m.p. 226°-229° C. Further concentration of the mother liquors yielded another 44.2 g of 5-acetyl-1,2-dihydro-6-methyl-2-oxonicotinonitrile, m.p. 221°-225° C.

A-6. 5-Acetyl-1,2-dihydro-4,6-dimethyl-2-oxonicotinonitrile—It is contemplated that this compound can be obtained following the procedure described in Example A-1 using in place of dimethylformamide dimethyl acetal a molar equivalent quantity of dimethylacetamide dimethyl acetal.

B. 5-(LOWER-ALKANOYL)-6-(LOWER-ALKYL)-1,2-DIHYDRO-2-OXONICOTINIC ACID

B-1. 5-Acetyl-1,2-dihydro-6-methyl-2-oxonicotinic Acid—A mixture containing 34 g of 5-acetyl-1,2-dihydro-6-methyl-2-oxonicotinamide, 50 ml of concentrated sulfuric acid and 100 ml of water was heated on a steam bath with stirring for 6 hours. The hot reaction solution was filtered and to the filtrate was added 50 ml of water.

The resulting mixture was allowed to stand at room temperature overnight whereupon the product crystallized out. The separated product was collected, washed with water, dried in a vacuum oven at 90°-95° C. to yield 16.8 g of 5-acetyl-1,2-dihydro-6-methyl-2-oxonicotinic acid, m.p. 238°-241° C. This acid was recrystallized from methanol and dried to yield 14.7 g of 5-acetyl-1,2-dihydro-6-methyl-2-oxonicotinic acid, m.p. 241°-243° C.

B-2. 6-Ethyl-1,2-dihydro-2-oxo-5-(n-propanoyl)nicotinic Acid—A mixture containing 40.8 g of 6-ethyl-1,2-dihydro-2-oxo-5-(n-propanoyl)nicotinonitrile, 50 ml of water, 75 ml of concentrated sulfuric acid and 200 ml of acetic acid was heated on a steam bath for 8 hours, cooled and concentrated on a rotary evaporator to remove the acetic acid and water. The remaining mixture was diluted with 300 ml of water and chilled for 1 hour in an ice bath. The white solid that separated was collected, washed with water and dried in a vacuum oven at 80° C. and recrystallized from isopropyl alcohol-ether and dried in a vacuum oven at 90° C. to yield 34.6 g of 6-ethyl-1,2-dihydro-2-oxo-5-(n-propanoyl)nicotinic acid, m.p. 180°-182° C.

B-3. 5-(n-Butanoyl)-1,2-dihydro-2-oxo-6-n-propylnicotinic acid, m.p. 183°-185° C., 19.4 g, was prepared following the procedure described in Example B-2 using 22 g of 5-(n-butanoyl)-1,2-dihydro-2-oxo-6-n-propylnicotinonitrile, 100 ml of acetic acid, 25 ml of concentrated sulfuric acid and 10 ml of water, a heating period of 75 hours on a steam bath and recrystallization of the product from isoproyl alcohol-n-hexane.

B-4. 5-Acetyl-1,2-dihydro-6-methyl-2-oxonicotinic Acid—A mixture containing 52.8 g of 5-acetyl-1,2-dihydro-6-methyl-2-oxonicotinonitrile, 150 ml of water and 75 ml of concentrated sulfuric acid was heated on a steam bath for 15 hours whereupon no reaction took place. The reaction mixture was then heated in a oil bath at 130°-140° C. for six hours allowing the water to form by the reaction to evaporate using an air-cooled condenser. The reaction mixture was allowed to stand at room temperature overnight whereupon a white crystalline solid separated. The solid was collected, washed with water and dried in a vacuum oven at 90°-95° C. to yield 49 g of 5-acetyl-1,2-dihydro-6-methyl-2-oxonicotinic acid, m.p. 239°-241° C. To the filtrate was added aqueous ammonia until the pH was about 4 and the solid that separated was collected, washed with water and dried in vacuo at 90°-95° C. to yield another 5.8 g of 5-acetyl-1,2-dihydro-6-methyl-2-oxonicotinic acid, m.p. 238°-241° C.

B-5. 5-Acetyl-1,2-dihydro-4,6-dimethyl-2-oxonicotinic Agent—It is contemplated that this compound can be obtained following the procedure described in Example B-4 but using in place of 5-acetyl-1,2-dihydro-6-methyl-2-oxonicotinonitrile a molar equivalent quantity of 5-acetyl-1,2-dihydro-4,6-dimethyl-2-oxonicotinonitrile.

C. 5-(LOWER-ALKANOYL)-6-(LOWER-ALKYL)-2(1H)-PYRIDINONES BY DECARBOXYLATION OF CORRESPONDING NICOTINIC ACIDS

C-1. 5-Acetyl-6-methyl-2(1H)-pyridinone—A 10 g portion of 5-acetyl-1,2-dihydro-6-methyl-2-oxonicotinic acid was heated neat in a bath of a boiling mixture of diphenyl and diphenyl ether for 40 minutes and the mixture allowed to cool to room temperature. The reaction mixture was dissolved in hot isopropyl alcohol, treated with decolorizing charcoal and filtered, and the filtrate allowed to stand at room temperature for several hours. The separated product was collected and dried at 90°-95° C. to yield 4.3 g of 5-acetyl-6-methyl-2-(1H)-pyridinone, m.p. 193°-195° C.

C-2. 6-Ethyl-5-(n-propanoyl)-2(1H)-pyridinone—A 15 g portion of 6-ethyl-1,2-dihydro-2-oxo-5-(n-propanoyl)nicotinic acid was heated in an oil bath at 235°-240° C. for 5 hours, cooled and the reaction mixture dissolved in hot ethanol, treated with decolorizing charcoal and filtered. The filtrate was evaporated in dryness and the residue recrystallized from isopropyl alcohol to yield 8.2 g of 6-ethyl-5-(n-propanoyl)-2(1H)-pyridinone, m.p. 138°-140° C.

C-3. 5-(n-Butanoyl)-6-n-propyl-2(1H)-pyridinone—A 12.5 g portion of 5-(n-butanoyl)-1,2-dihydro-2-oxo-6-n-propylnicotinic acid was heated in an oil bath at 240°-245° C. for 3 hours, cooled and the oily residue crystallized from n-hexane after washing with cold aqueous sodium bicarbonate solution to yield 3.8 g of 5-(n-butanoyl)-6-n-propyl-2(1H)-pyridinone, m.p. 86°-88° C.

C-4. 5-Acetyl-4,6-dimethyl-2(1H)-pyridinone—It is contemplated that this compound can be obtained following the procedure described in Example C-1 using in place of 5-acetyl-1,2-dihydro-6-methyl-2-oxonicotinic acid a molar equivalent quantity of 5-acetyl-1,2-dihydro-4,6-dimethyl-2-oxonicotinic acid.

D. 5-(LOWER-ALKANOYL)-6-(LOWER-ALKYL)-2(1H)-PYRIDINONES BY DIRECT SYNTHESIS

D-1. 5-Acetyl-6-methyl-2(1H)-pyridinone—A mixture containing 100 g of 2,4-pentanedione, 200 ml of ethanol and 60 ml of a concentrated aqueous ammonium hydroxide was allowed to stand at room temperature over the weekend (3 days) and then concentrated on a rotary evaporator to yield 83 g of 4-amino-3-penten-2-one as an oil. To the stirred oil was added 70 ml of methyl 2-propynoate over a 10 minute period and the resulting solution was stirred at ambient temperature for 30 minutes whereupon a vigorous exothermic reaction took place. After the exothermic reaction had subsided, the reaction mixture was heated on a steam bath for 2.5 hours, the reaction mixture was then dissolved in 300 ml of boiling isopropyl alcohol, the solution treated with decolorizing charcoal and filtered, and the filtrate concentrated on a rotary evaporator to yield a viscous liquid. To the viscous liquid was added 300 ml of ether and the mixture triturated and allowed to stand at room temperature overnight. The separated solid was collected, washed with ether and dried to yield 84.6 g of material whose NMR spectram indicated it to be the uncyclized intermediate, methyl 4-acetyl-5-amino-2,4-hexadienoate. [In another run this compound was isolated, recrystallized from methanol and found to melt at 104°-106° C.] The mother liquor from the above was concentrated on a rotary evaporator to a constant weight of 45.6 9 of dark oil. The oil was combined with the uncyclized material and dissolved in 250 ml of dimethylformamide and the resulting mixture was refluxed for 4.5 hours. The reaction mixture was allowed to stand at room temperature overnight whereupon the crystalline product separated. The crystalline precipitate was collected, washed with isopropyl alcohol, dried in a vacuum oven at 90°-95° C. to yield 62.5 g of 5-acetyl-6-methyl-2(1H)-pyridinone, m.p. 196°-198° C. The mother liquor from the above was concentrated to dryness on a rotary evaporator and the residue dissolved in 100 ml of isopropyl alcohol, the alcohol solution treated with decolorizing charcoal and filtered and the filtrate allowed to stand at room temperature overnight. The precipitate that separated was collected to yield another 15.2 g of 5-acetyl-6-methyl-2(1H)-pyridinone, m.p. 194°-196° C.

D-2. 6-Methyl-5-(n-propanoyl)-2(1H)-pyridinone—A mixture containing 25 g of 2,4-hexanedione, 100 ml of ethanol and 25 ml of concentrated aqueous ammonium hydroxide was allowed to stand room temperature overnight and then concentrated on a rotary evaporator to give 21 g, as a pale yellow oil, a mixture containing 4-amino-3-hexen-2-one and 5-amino-4-hexen-3-one. To the oil was added 18.5 g of methyl, 2-propynoate and the mixture heated in a oil bath at about 100° whereupon a vigorous exothermic reaction took place. After the reaction had subsided, the reaction mixture was heated in an oil bath at 160°-170° C. for 2 hours and then concentrated on a rotary evaporator to give a gummy material. The latter was crystallized from isopropyl alcohol-ether to yield 64 g of 6-methyl-5-(n-propanoyl)-2(1H)-pyridinone, m.p. 173°-175° C., whose structure was confirmed by its NMR spectrum. No other product was isolated from the mother liquor of the above reaction mixture; however, in another run, Example D-4 hereinbelow, a second product, namely 6-ethyl-5-acetyl-2(1H)-pyridinone was isolated.

D-3. 5-Acetyl-4,6-dimethyl-2(1H)-pyridinone—A mixture containing 40 g of 2,4-pentanedione, 100 ml of ethanol and 50 ml of concentrated aqueous ammonium hyroxide was allowed to stand at room temperature for 6 hours and then concentrated on a rotary evaporator to yield, as an oil, 35.4 g of 4-amino-3-penten-2-one. The oil was dissolved in 100 ml of dimethylformamide and to the solution was added 32 g of methyl 2-butynoate and the resulting reaction mixture was refluxed for 95 hours and then concentrated on a rotary evaporator. The remaining oil residue was heated with 100 ml of ether whereupon a white solid crystallized spontaneously. The solid was collected, washed with ether and dried in a vacuum oven at 90°-95° C. to yield 25.7 g of 5-acetyl-4,6-dimethyl-2(1H)-pyridinone, m.p. 160°-162° C.

D-4. 6-Methyl-5-(n-propanoyl)-2(1H)-pyridinone and 5-Acetyl-6-ethyl-2(1H)-pyridinone—A mixture containing 50 g of 2,4-hexanedione, 100 ml of ethanol and 50 ml of concentrated aqueous ammonium hydroxide was allowed to stand at room temperature overnight and then concentrated on a rotary evaporator at 50°-60° C. to a constant weight of 48.8 g, a pale yellow oil that solidified on standing at room temperature. The nmr spectrum of this solid in $CDCl_3$ indicated it to be a mixture of 5-amino-4-hexen-3-one and 4-amino-3-hexen-2-one in a weight ratio of 65:35. The mixture of amino-hexen-ones was dissolved in 100 ml of dimethylformamide and treated with methyl 2-propynoate and the resulting mixture was first gently heated with stirring on a steam bath for 2 hours and then refluxed for 24 hours. The reaction mixture was allowed to cool to room temperature and allowed to stand at room temperature overnight. The crystalline material that separated was collected, washed with isopropyl alcohol and dried in vacuo at 90°-95° C. to yield 11.9 g of 6-methyl-5-(n-propanoyl)-2(1H)-pyridinone, m.p. 173°-175° C. The mother liquor was concentrated on a rotary evaporator and the residue was crystallized from isopropyl alcohol, washed with ether and dried to yield another 10.4 g of 6-methyl-5-(n-propanoyl)-2(1H)-pyridinone, m.p. 173°-175° C. The filtrate was concentrated in vacuo to yield 57.8 g of an oily residue which was chromatographed on silica gel (700 g) using ether as eluant. Evaporation of the ether fractions yielded 22.4 g of the least polar component, an oily material, a middle fraction of 16.4 g, a viscous gummy oil, and as the most polar component, 7.8 g, a solid which was recrystallized from isopropyl alcohol to yield a white amorphous powder, m.p. 140°-145° C., whose nmr spectrum showed it to consist of 90% 5-acetyl-6-ethyl-2(1H)-pyridinone. Six further recrystallizations of this product resulted in 1.5 g of pure 5-acetyl-6-ethyl-2(1H)-pyridinone, m.p. 162°-164° C., as shown by its nmr spectrum.

D-5. 5-(n-Butanoyl)-6-methyl-2(1H)-pyridinone—A mixture containing 22.2 g of 3-methyl-5-n-propylisoxazole [Kashima et al., Bull. Chem. Soc. Japan 46, 310-313 (1973)], 500 mg of platinum dioxide and 200 ml of ethanol was hydrogenated under catalytic hydrogenation conditions for ninety minutes, the catalyst was filtered off and the filtrate was concentrated on a rotary evaporator to yield 18.5 g of colorless residue which solidified on cooling. The residue containing 2-amino-2-hepten-4-one was dissolved in 50 ml of dimethylformamide and to the solution was added 14.8 g of methyl 2-propynoate. The resulting reaction solution was allowed to stand at ambient temperature for thirty minutes (exothermic) and then refluxed for three and one half hours. The dimethylformamide was removed on a rotary evaporator. The remaining dark brown liquid was heated in an oil bath at 195°-200° C. for four hours, cooled to room temperature, crystallized from isopropyl alcohol and dried at 80°-85° C. to produce, as pale yellow flakes, 9.4 g of 5-(n-butanoyl)-6-methyl-2(1H)-pyridinone, m.p. 167°-168° C.

Following the procedure described in Example D-5 using in place of 3-methyl-5-n-propylisoxazole a molar equivalent quantity of the appropriate 3-methyl-5-R-isoxazole, it is contemplated that the 5-(RCO)-6-methyl-2(1H)-pyridinones of Examples D-6 and D-7 can be prepared via the appropriate 2-amino-2-alken-4-one.

D-6. 6-Methyl-5-(n-pentanoyl)-2(1H)-pyridinone, first using 5-n-butyl-3-methylisoxazole and then 2-amino-2-octen-4-one.

D-7. 6-Methyl-5-(3-methylpropanoyl)-2(1H)-pyridinone, first using 5-isopropyl-3-methylisoxazole and then 2-amino-5-methyl-2-hexen-4-one.

The usefulness of the compounds of formula I or III or methyl 4-acetyl-5-amino-2,4-hexadienoate as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with lower or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of formula I or III at doses of 1, 10, 30 and/or 100 μg/ml., were found to cause significant increases, that is, greater than 25% (cat) or 30% (g.pig) in papillary muscle force and significant increases, that is, greater than 25% (cat) or 30% (g.pig) in right atrial force, while causing a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, when tested by said guinea pig atria and papillary muscle procedure, the following illustrative compounds were found to cause respective papillary muscle force and right atrial force increases as follows: Example D-2, 39% and 35% at 1 μg/ml, 103% and 85% at 3 μg/ml, 120% and 107% at 10 μg/ml; Example C-1, 95% and 66% at 10 μg/ml, 109% and 114% at 30 μg/ml and 164% and 229% at 100 μg/ml; Example C-2, 77% and 78% at 10 μg/ml, 103% and 132% at 30 μg/ml and 160% and 374% at 100 μg/ml; Example D-3, 83% and 56% at 100 μg/ml; Example D-4 (5-acetyl-6-ethyl-2(1H)-pyridinone), 86% and 37% at 10 μg/ml and 146% and 40% at 30 μg/ml; Example D-5, 65% and 115% at 1 μg/ml, 92% and 183% at 3 μg/ml and 145% and 237% at 10 μg/ml. Example A-2, 101% and 56% at 10 μg/ml, 164% and 111% at 30 μg/ml; Example A-4, 57% and 55% at 30 μg/ml and 128% and 146% at 100 μg/ml; Example A-3, 72% and 82% at 30 μg/ml and 136% and 131% at 100 μg/ml; and Example A-1, 90% and 41% at 30 μg/ml and 82% and 105% at 100 μg/ml. When tested by said guinea pig atria and papillary muscle procedure, methyl 4-acetyl-5-amino-2,4-hexadienoate was found to cause papillary muscle force and right atrial force increases of 55% and 279% respectively at 100 μg/ml.

When tested by said anesthetized dog procedure, the compounds of formula I or III at doses of 0.03, 0.10, 0.30, 1.0 and/or 3.0 mg/kg administered intravenously were found to cause significant increases, that is, 25% or greater, in cardiac contractile force or cardiac contractility with lower changes in heart rate and blood pressure. For example, when tested at one or more of said dose levels by this procedure, the compounds of Examples C-1, C-2, A-2, A-4, D-2, D-4 and D-5 were found to cause increases of 36% to 218% in contractile force with lower changes in heart rate and blood pressure.

The present invention includes within its scope a cardiotonic composition for increasing cardiac contractility, said composition comprising a pharmaceutically acceptable carrier and, as the active component thereof, the compound of formula III. The invention also includes within its scope the method for increasing cardiac contractility in a patient requiring such treatment which comprises administering to such patient a cardiotonically effective amount of the compound of formula III. In clinical practice said compound will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic ester such as ethyl oleate. These compositions can also contain adjuvants such as stabilizing, preserving, wetting, emulsifying and dispersing agents.

They can be sterilized, for example by filtration through a bacterial-retaining filter, by incorporation of sterilizing agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied to that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. A 5-(lower-alkanoyl)-6-(lower-alkyl)-2(1H)-pyridinone having the formula

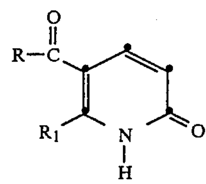

where R and $R_1$ are each lower-alkyl.

2. A compound according to claim 1 where $R_1$ is methyl or ethyl and R is methyl, ethyl or propyl.

3. 5-Acetyl-6-methyl-2(1H)-pyridinone according to claim 1.

4. 6-Methyl-5-(n-propanoyl)-2(1H)-pyridinone according to claim 1.

5. 6-Ethyl-5-(n-propanoyl)-2(1H)-pyridinone according to claim 1.

6. 5-Acetyl-6-ethyl-2(1H)-pyridinone according to claim 1.

7. 5-n-Butanoyl-6-methyl-2(1H)-pyridinone according to claim 1.

8. A cardiotonic composition for increasing cardiac contractility, said composition comprising a pharmaceutically acceptable inert carrier and, as the active component thereof, a cardiotonically effective amount of 5-(lower-alkanoyl)-6-(lower-alkyl)-2(1H)pyridinone having the formula

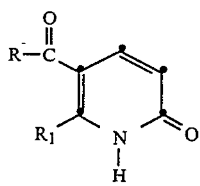

where R and $R_1$ are each lower-alkyl.

9. A composition according to claim 8 where the active component is 5-acetyl-6-methyl-2(1H)-pyridinone.

10. A composition according to claim 8 where the active component is 6-methyl-5-(n-propanoyl)-2(1H)-pyridinone.

11. A composition according to claim 8 where the active component is 6-ethyl-5-(n-propanoyl)-2(1H)-pyridinone.

12. A composition according to claim 8 where the active component is 5-acetyl-6-ethyl-2(1H)-pyridinone.

13. The method for increasing cardiac contractility in a patient requiring such treatment which comprises administering orally or parenterally in a solid or liquid dosage form to such patient a cardiotonic composition comprising a pharmaceutically acceptable inert carrier and, as the active component thereof, a cardiotonically effective amount of 3-Q-4-$R_2$-5-(lower-alkanoyl)-6-(lower-alkyl)-2(1H)pyridinone having the formula

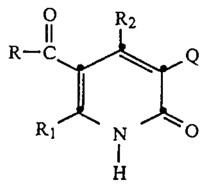

where Q is hydrogen or cyano, R and $R_1$ are each lower-alkyl and $R_2$ is hydrogen or methyl.

14. A method according to claim 13 where the active component is 5-acetyl-6-methyl-2(1H)-pyridinone.

15. A method according to claim 13 where the active component is 6-methyl-5-(n-propanoyl)-2(1H)-pyridinone.

16. A method according to claim 13 where the active component is 6-ethyl-5-(n-propanoyl)-2(1H)-pyridinone.

17. A method according to claim 13 where the active component is 5-acetyl-6-ethyl-2(1H)-pyridinone.

18. A cardiotonic composition for increasing cardiac contractility, said composition comprising a pharmaceutically acceptable inert carrier and, as the active component thereof, a cardiotonically effective amount of 6-ethyl-1,2-dihydro-2-oxo-5-(n-propanoyl)-nicotinonitrile.

19. The method for increasing cardiac contractility in a patient requiring such treatment which comprises administering orally or parenterally in a solid or liquid dosage form to such patient a cardiotonically effective amount of the active component of claim 18.

* * * * *